United States Patent
Ota et al.

(10) Patent No.: US 9,470,607 B2
(45) Date of Patent: Oct. 18, 2016

(54) METHOD FOR PRODUCING STANDARD SEAWATER SOLUTION FOR NUTRIENT SALT MEASUREMENT

(75) Inventors: Hidekazu Ota, Osaka (JP); Hitoshi Mitsuda, Osaka (JP); Munehito Kimura, Osaka (JP); Takashi Kitao, Osaka (JP)

(73) Assignee: The General Environmental Technos Co., Ltd., Osaka (JP)

( * ) Notice: Subject to any disclaimer, the term of this patent is extended or adjusted under 35 U.S.C. 154(b) by 617 days.

(21) Appl. No.: 13/981,363

(22) PCT Filed: Feb. 10, 2011

(86) PCT No.: PCT/JP2011/052895
§ 371 (c)(1),
(2), (4) Date: Jul. 24, 2013

(87) PCT Pub. No.: WO2012/108038
PCT Pub. Date: Aug. 16, 2012

(65) Prior Publication Data
US 2013/0305660 A1    Nov. 21, 2013

(51) Int. Cl.
  *B65B 55/08*    (2006.01)
  *B65B 55/12*    (2006.01)
  *G01N 1/00*    (2006.01)
  (Continued)

(52) U.S. Cl.
  CPC .................. *G01N 1/00* (2013.01); *B65B 55/08* (2013.01); *B65B 55/12* (2013.01); *G01N 1/18* (2013.01); *G01N 1/28* (2013.01); *G01N 33/18* (2013.01);
  (Continued)

(58) Field of Classification Search
  CPC ............ G01N 1/00; G01N 1/18; G01N 1/28; G01N 1/2806; G01N 33/18; G01N 2001/2893; C02F 1/30; C02F 1/32; C02F 2209/05; C02F 2103/08
  See application file for complete search history.

(56) References Cited

U.S. PATENT DOCUMENTS 4,116,336 A    9/1978   Sorensen et al.
4,151,108 A    4/1979   Sørensen et al.
(Continued)

FOREIGN PATENT DOCUMENTS

JP    58-193461    11/1983
JP    10-236442    9/1998
(Continued)

OTHER PUBLICATIONS

Machine translation of JP 2003-214996 to Ota (obtaind from JPO Mar. 2016).*
(Continued)

*Primary Examiner* — Lucas Stelling
(74) *Attorney, Agent, or Firm* — Wenderoth, Lind & Ponack, L.L.P.

(57) ABSTRACT

A method of producing a standard seawater solution for nutrient salt measurement includes at least: an impurity removal treatment step (S2) of removing an impurity from a seawater sample containing a nutrient salt; a main sterilization treatment step (S4) of killing a microorganism in the seawater sample; a bottling step (S6) including pouring the treated seawater sample into a resin bottle (3) and hermetically sealing the resin bottle; and a metal sealing step (S7) including covering an outer surface of the resin bottle (3) after the hermetic sealing with a film-like material (5) including a metal film (or a metal foil) (5a) and sealing the resin bottle therein by reduced pressure suction.

4 Claims, 4 Drawing Sheets

(51) Int. Cl.
  *G01N 1/18* (2006.01)
  *G01N 1/20* (2006.01)
  *G01N 33/18* (2006.01)
  *G01N 1/28* (2006.01)

(52) U.S. Cl.
  CPC ............... *G01N 2001/2071* (2013.01); *G01N 2001/2893* (2013.01)

(56) References Cited

U.S. PATENT DOCUMENTS

| | | | |
|---|---|---|---|
| 4,163,734 A | 8/1979 | Sørensen et al. | |
| 4,588,554 A | 5/1986 | Kaartinen et al. | |
| 5,777,202 A * | 7/1998 | Betts | B01L 3/505 73/1.03 |
| 6,338,235 B1 * | 1/2002 | Bentz | A61L 2/208 53/140 |
| 2008/0065043 A1 * | 3/2008 | Bemer | A61J 1/10 604/408 |

FOREIGN PATENT DOCUMENTS

| | | |
|---|---|---|
| JP | 11-060401 | 3/1999 |
| JP | 2000-175989 | 6/2000 |
| JP | 2003-214996 | 7/2003 |
| JP | 3477468 | 12/2003 |
| JP | 2006-058080 | 3/2006 |
| JP | 2008-512160 | 4/2008 |
| JP | 2009-031231 | 2/2009 |
| JP | 4459752 | 4/2010 |

OTHER PUBLICATIONS

International Preliminary Report on Patentability and Written Opinion of the International Searching Authority mailed Aug. 22, 2013 in International (PCT) Application No. PCT/JP2011/052895.

International Search Report mailed Apr. 12, 2011 in International (PCT) Application No. PCT/JP2011/052895.

Alian Aminot, Roger Kérouel, "Stability and Preservation of Primary Calibration Solutions of Nutrients", Marine Chemistry, Apr. 1996, vol. 52, No. 2, pp. 173-181.

Hidekazu Ota et al., "Comparability of Nutrients in the World Ocean", INSS International Workshop, Aug. 21, 2010, pp. 11 and 22-25.

* cited by examiner

METHOD FOR PRODUCING STANDARD SEAWATER SOLUTION FOR NUTRIENT SALT MEASUREMENT

BACKGROUND OF INVENTION

1. Field of Invention

The present invention relates to a method of producing a standard seawater solution for nutrient salt measurement to be used as an indicator for measuring a nutrient salt concentration in seawater for a purpose of an oceanographic survey or the like.

2. Description of Related Art

As is well known, when an oceanographic survey or the like is conducted, there may be given measurement of a nutrient salt concentration in seawater as a basic item. In that case, in order to collect measurement data regarding a concentration of a nutrient salt in actual seawater as a sample, it is convenient to produce and use a standard seawater solution for nutrient salt measurement as an indicator. Note that the nutrient salt as used herein refers to salts required for producing microorganisms, for example, salts such as a nitrate, a nitrite, a phosphate, a silicate, and an ammonium salt.

As this type of standard seawater solution for nutrient salt measurement (hereinafter also referred to simply as "standard seawater solution"), there may be given one produced through use of seawater as a material as disclosed in JP 3477468 B2 described below. In addition, JP 3477468 B2 discloses a method of producing a standard seawater solution through use of seawater as a material comprising, as basic steps, a filtering treatment step of filtering a plurality of kinds of material seawater having different nutrient salt concentrations collected from places at different water depths in a predetermined sea area, a mixing treatment step of mixing the plurality of kinds of material seawater in a predetermined ratio, and a sterilization treatment step of killing microorganisms in the material seawater by heating or the like.

Further, JP 3477468 B2 discloses that the method of producing a standard seawater solution further comprises a bottling step comprising pouring the treated seawater after the above-mentioned sterilization treatment into a resin bottle and hermetically sealing the resin bottle in a clean environment and a sealing step comprising covering an outer surface of the hermetically sealed resin bottle with a film-like material and sealing the resin bottle therein by reduced pressure suction.

Further, JP 4459752 B2 described below discloses that, when seawater containing nutrient salts is subjected to sterilization treatment including at least heating treatment while being stored in a large-capacity container, the seawater containing nutrient salts is subjected to the sterilization treatment while being stored in a large-capacity container made of metal having an electrolytically-polished inner surface. In addition, JP 4459752 B2 also discloses that the bottling step and the sealing step are performed after the sterilization treatment in the same way as the above.

According to the production methods disclosed in JP 3477468 B2 and JP 4459752 B2, it is possible to obtain a standard seawater solution of good quality as an indicator for measuring the concentration of a nutrient salt in actual seawater as a sample, and it can be expected that the production methods are useful for an appropriate oceanographic survey and the like.

TECHNICAL PROBLEM

However, even the above-mentioned methods for producing a standard seawater solution disclosed in JP 3477468 B2 and JP 4459752 B2 still have problems to be solved from the viewpoint of appropriately ensuring properties which a standard seawater solution should originally have.

That is, the standard seawater solution is not always used for an oceanographic survey or the like immediately after the production and is used in many cases after being stored for a long period of time such as several years. The inventors of the present invention conducted research, paying attention to such circumstances, and found the following: the salt content (meaning salt concentration, the same applies hereinafter) and nutrient salt concentration of the standard seawater solution increase along with the passage of a storage period, and if the storage is prolonged, an improper deviation is caused in a balance of the salt content and nutrient salt concentration of the standard seawater solution.

In view of the foregoing, the inventors of the present invention investigated the reason for the occurrence of such situation and found that, of the respective steps of the production methods disclosed in JP 3477468 B2 and JP 4459752 B2, the sealing step is greatly involved in the occurrence of such situation. Then, the inventors of the present invention further conducted research, and as a result, found that the occurrence of such situation as described above is caused by the following: a resin bottle with a standard seawater solution sealed therein is conventionally subjected to vacuum packing (sealing by reduced pressure suction) while the outer surface of the resin bottle is covered with a film made of polyethylene or a resin similar thereto in the sealing step.

Thus, as a result of the extensive research by the inventors of the present invention, it was found that the following problem occurs: if the sealing step is performed by the above-mentioned procedure, a standard seawater solution stored for a long period of time becomes unsuitable as an indicator for measuring a nutrient salt concentration of an actual seawater sample in an oceanographic survey or the like due to significant changes in salt content and nutrient salt concentration and becomes a factor for inducing a measurement error, and hence the standard seawater solution cannot be used.

Further, the inventors of the present invention also found that, although the standard seawater solution is subjected to the sterilization treatment step of killing microorganisms in seawater by heating or the like as disclosed in JP 3477468 B2 and JP 4459752 B2, the nutrient salt concentration decreases against the expectation while the standard seawater solution is stored (for a long period of time). The inventors of the present invention also investigated the reason for the foregoing and found that, of the respective steps of the above-mentioned production methods, a resin bottle to be used for performing the bottling step is greatly involved in the above-mentioned decrease in nutrient salt concentration.

Then, the inventors of the present invention further conducted research, and as a result, found the reason for the occurrence of such situation. That is, a resin bottle to be used in the bottling step is conventionally washed through use of pure water, a cleaning liquid or the like in a clean room and packed in a bag; however, with such procedure, the adhesion of microorganisms to the inner surface of the resin bottle cannot be avoided completely.

Thus, as a result of the extensive research by the inventors of the present invention, it was found that the following problem occurs: if the resin bottle is only washed by the above-mentioned procedure, the microorganisms adhering to the inner surface of the bottle propagate in the standard seawater solution sealed in the bottle during storage to decrease the nutrient salt concentration, and hence the standard seawater solution becomes unsuitable as an indicator for measuring a nutrient salt concentration of an actual seawater sample in an oceanographic survey or the like and cannot be used.

SUMMARY OF INVENTION

From the foregoing viewpoints, it is an object of the present invention to appropriately maintain properties which a standard seawater solution for nutrient salt measurement should originally have without causing the properties to change even after long-term storage.

SOLUTION TO PROBLEM

The present invention devised to achieve the object is a method of producing a standard seawater solution for nutrient salt measurement which is to be used as an indicator for measuring a nutrient salt concentration of a seawater sample and which uses seawater as a material, the method comprising at least: an impurity removal treatment step of removing an impurity from a seawater sample containing a nutrient salt; a main sterilization treatment step of killing a microorganism in the seawater sample; a bottling step comprising pouring the treated seawater sample into a resin bottle and hermetically sealing the resin bottle; and a sealing step comprising covering an outer surface of the resin bottle after being hermetically sealed with a film-like material and sealing the resin bottle therein by reduced pressure suction, wherein the sealing step comprises covering the outer surface of the resin bottle after being hermetically sealed with a film-like material including a metal film or a metal foil and sealing the resin bottle therein surface by reduced pressure suction. In this case, the impurity removal treatment step is performed before or after the main sterilization treatment step is performed, or before and after the main sterilization treatment step is performed, and is performed during a period until the treated seawater is poured into the bottle in the bottling step.

According to the above-mentioned method, treated seawater obtained by subjecting a seawater sample containing a nutrient salt to at least the impurity removal treatment and the main sterilization treatment, that is, a standard seawater solution immediately after generation, is poured into a bottle made of a resin such as polypropylene and hermetically sealed therein in the bottling step, and thereafter, the outer surface of the bottle is covered with a film-like material including a metal film or a metal foil and the resin bottle is sealed therein by reduced pressure suction (so-called vacuum packing) in the sealing step. In this case, the metal film or the metal foil is excellent in light-blocking property, moisture-proof property, and gas barrier property and has property of preventing moisture from leaking outside. Therefore, even when the standard seawater solution sealed in the bottle after the sealing step is finished is stored for a long period of time such as several years, its salt content and nutrient salt concentration hardly change. Thus, even when the standard seawater solution stored for a long period of time is used as an indicator for measuring a nutrient salt concentration of an actual seawater sample in an oceanographic survey or the like, the nutrient salt concentration of the seawater sample can be measured correctly without inducing an error. Note that it is preferred that the film-like material have a bag shape.

In this method, it is preferred that the metal film or the metal foil of the film-like material comprise an aluminum film or an aluminum foil.

With the above-mentioned configuration, of the metal film or the metal foil, the aluminum film or the aluminum foil is excellent in property of preventing moisture from leaking outside, and aluminum is also excellent in strength and flexibility in the case of being formed as a film or a foil. Hence, sealing property by the reduced pressure suction is enhanced and changes in salt content and nutrient salt concentration caused by long-term storage of the standard seawater solution becomes remarkably unlikely to occur. Note that, even when a film or a foil of copper or nickel, or a metal similar thereto is used as the metal film or the metal foil, a sufficient effect regarding the long-term storage of the standard seawater solution can be obtained.

In the above-mentioned method, it is preferred that the metal film or the metal foil of the film-like material cover an entire outer surface of the resin bottle.

That is, although the metal film or the metal foil of the film-like material may cover the outer surface of only a main portion such as a body portion of the resin bottle, the above-mentioned effect regarding the long-term storage of the standard seawater solution can be obtained if the metal film or the metal foil covers the entire outer surface.

In the above-mentioned method, it is preferred that the film-like material have a multi-layer structure in which a resin material is provided on each of both front and back sides of the metal film or the metal foil.

With the above-mentioned configuration, each of both the front and back sides of the metal film or the metal foil is covered with a resin material, and hence the metal film or the metal foil is unlikely to be, for example, broken or torn during the reduced pressure suction, and the function regarding the stability of the salt content and the nutrient salt concentration can be exhibited sufficiently. Note that, in order to form the film-like material as such multi-layer structure, a procedure involving coating a metal foil with a resin or forming a metal film on the surface of a resin film by vapor deposition or the like is adopted. As the resin material in this case, there may be given a polymer film such as a PET film (polyethylene terephthalate).

The present invention devised to achieve the object is also a method of producing a standard seawater solution for nutrient salt measurement which is to be used as an indicator for measuring a nutrient salt concentration of a seawater sample and which uses seawater as a material, the method comprising at least: an impurity removal treatment step of removing an impurity from a seawater sample containing a nutrient salt; a main sterilization treatment step of killing a microorganism in the seawater sample; and a bottling step comprising pouring the treated seawater sample into a resin bottle and hermetically sealing the resin bottle, wherein before the bottling step is performed, at least an entire inner surface of the resin bottle is sterilized with ultraviolet rays. Also in this case, the impurity removal treatment step is performed before or after the main sterilization treatment step is performed, or before and after the main sterilization treatment step is performed, and is performed during a period until the treated seawater is poured into the bottle in the bottling step.

According to the above-mentioned method, in the case where treated seawater obtained by subjecting a seawater sample containing a nutrient salt to at least the impurity removal treatment and the main sterilization treatment, that is, a standard seawater solution immediately after generation, is poured into a bottle made of a resin such as polypropylene and hermetically sealed therein in the bottling step, at least the entire inner surface of the bottle has already been subjected to the sterilization treatment with ultraviolet rays before the bottling step is performed, and thus microorganisms have been killed. Therefore, there are no microorganisms adhering to the inner surface of the bottle, and hence the following inconvenience is avoided: microorganisms propagate in the standard seawater solution sealed in the bottle to decrease a nutrient salt concentration. As a result, even in the case where the standard seawater solution is sealed in the bottle to be stored for a long period of time, the nutrient salt concentration becomes unlikely to change. Therefore, the standard seawater solution can be used appropriately for a long period of time as a correct indicator for measuring a nutrient salt concentration of an actual seawater sample in an oceanographic surveyor the like.

ADVANTAGEOUS EFFECTS OF INVENTION

As described above, according to the present invention, in the standard seawater solution for nutrient salt measurement immediately after generation at least after the impurity removal treatment and the main sterilization treatment are performed, its salt content and nutrient salt concentration become unlikely to change during its storage. Therefore, a standard seawater solution for nutrient salt measurement of good quality, which is constantly stable, can be ensured even when stored for a long period of time, and a nutrient salt concentration of a seawater sample can be constantly measured correctly.

DESCRIPTION OF EMBODIMENTS

A method of producing a standard seawater solution for nutrient salt measurement according to an embodiment of the present invention is described below with reference to the attached drawings.

Figure 1:
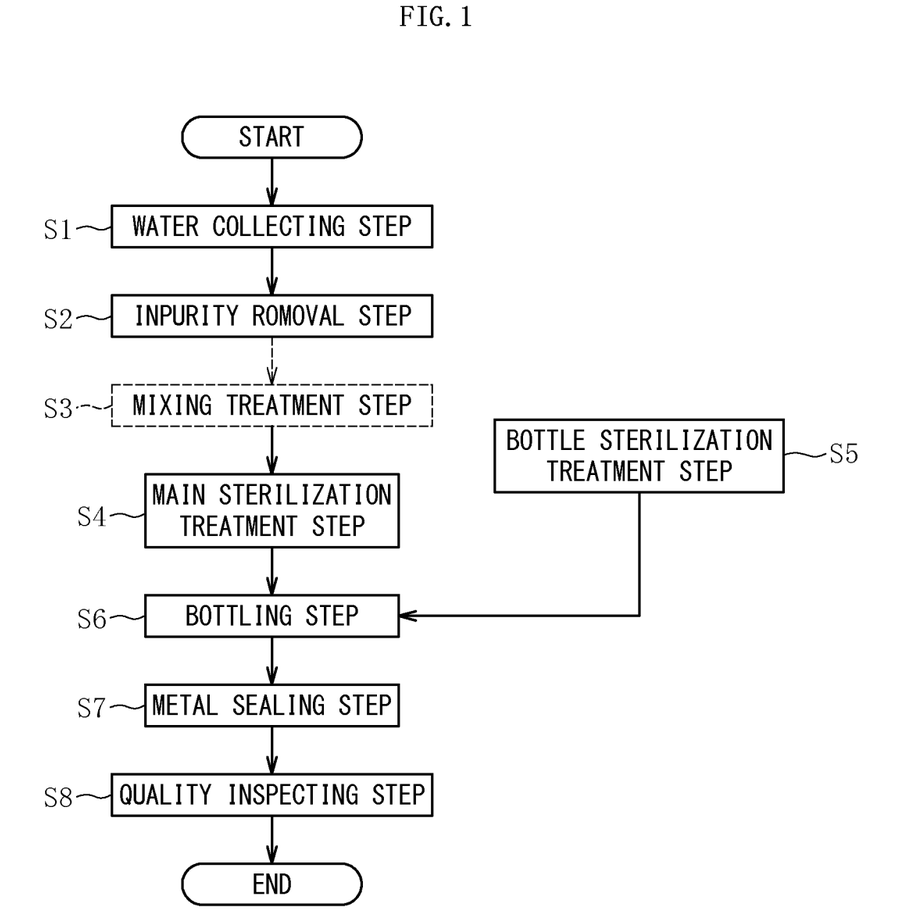
FIG. 1 is a flowchart illustrating a procedure for a method of producing a standard seawater solution for nutrient salt measurement according to an embodiment of the present invention.

FIG. 1 is a flowchart illustrating a procedure for the method of producing a standard seawater solution according to the embodiment of the present invention. As illustrated in FIG. 1, in the production method, first, actual seawater in a predetermined sea area is collected in a water collecting step S1, and the collected seawater serves as a material for a standard seawater solution. In this case, as necessary, at least two kinds of seawater (for example, deep-water and surface water) are collected from places at different water depths in a predetermined sea area, but only one kind of seawater may be collected.

A subsequent impurity removal step S2 is a step of removing impurities from the collected seawater and involves, for example, removing impurities by collecting them through use of a filter or removing impurities by separating them from seawater by centrifugation. Note that the impurities as used herein refer to, for example, microorganisms such as plankton, algae, or colloidal chemical substances, or substances similar thereto.

A subsequent mixing treatment step S3 is a step of adjusting a nutrient salt concentration by mixing at least two kinds of seawater in a predetermined ratio in the case of assuming that at least two kinds of seawater are collected in the water collecting step S1. The mixing treatment step S3 is not necessarily required, and the mixing treatment step S3 may not be performed, for example, in the case of collecting one kind of seawater.

A subsequent main sterilization treatment step S4 is a step of killing microorganisms in the collected seawater, and is performed for preventing a nutrient salt concentration in the collected seawater from decreasing due to the propagation of microorganisms. As the main sterilization treatment, there may be given, for example, heating treatment, filtering treatment, irradiation of a radiation, and mixing of a toxic substance such as mercury. From the viewpoints of, for example, safety and convenience, it is preferred to adopt the heating treatment. In addition, the main sterilization treatment step S4 is performed by storing seawater in a large-capacity tank.

In this case, in a previous stage before a subsequent bottling step S6 is performed, a bottle sterilization treatment step S5 is separately performed. The bottle sterilization treatment step S5 is a step of sterilizing at least the entire inner surface of a small-capacity resin bottle, into which treated seawater (standard seawater solution immediately after generation) after the main sterilization treatment is performed is poured from the large-capacity tank, to the bottle irradiated with ultraviolet rays. The bottle sterilization treatment step S5 is performed with respect to a plurality of empty bottles.

The bottling step S6 is a step of pouring the treated seawater into the resin bottle subjected to the sterilization treatment from the large-capacity tank and hermetically sealing the bottle, and for example, the bottling step S6 is performed with respect to a plurality of bottles from one large-capacity tank.

Note that the impurity removal step S2 may be further performed after the main sterilization treatment step S4, and may also be performed only after the main sterilization treatment step S4. In any case, it is appropriate that the impurity removal step S2 be performed in the previous stage before the bottling step S6 (including the case of filtering the treated seawater through use of a filter when pouring the treated seawater into the bottle from the large-capacity tank in the bottling step S6).

A subsequent metal sealing step s7 is a step of covering the outer surface of the hermetically sealed bottle with a film-like material (preferably a bag formed of a film) including a metal film or a metal foil and sealing the outer surface by reduced pressure suction. It is preferred that the metal film or the metal foil be an aluminum film or an aluminum foil.

A subsequent quality inspecting step S8 is a step of collecting a predetermined number of standard seawater solutions at random from the standard seawater solutions produced as described above, measuring each nutrient salt concentration to confirm that a deviation in a lot is small, and attaching information on each standard seawater solution to the surface of the film-like material.

Figure 2:
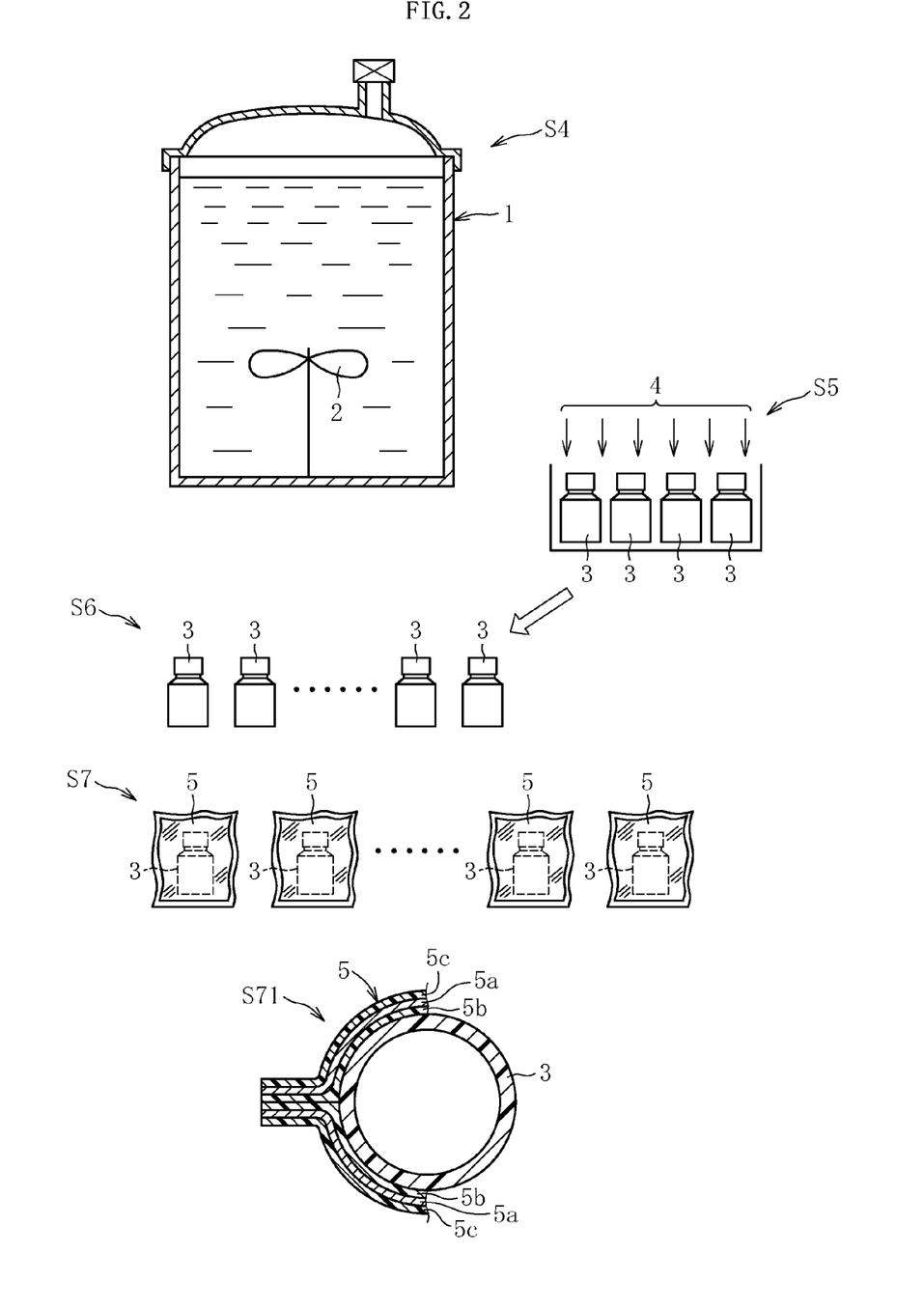
FIG. 2 is a schematic view illustrating performed states of main steps of the method of producing a standard seawater solution for nutrient salt measurement according to the embodiment of the present invention.

FIG. 2 is a schematic view illustrating the performed states of the method of producing a standard seawater solution according to the embodiment, and illustrating only the performed states of main steps of the respective steps S1 to S8 of the production method. More specifically, FIG. 2 illustrates the performed states of the main sterilization treatment step S4, the bottle sterilization treatment step S5, the bottling step S6, and the metal sealing step S7.

As indicated by reference symbol S4 in FIG. 2, collected material seawater (subjected to the impurity removal treatment if necessary) is stored in a large-capacity tank 1 made of metal, and the material seawater contains nutrient salts required for producing microorganisms, such as a nitrate, a nitrite, a phosphate, a silicate, and an ammonium salt. Then, the material seawater is heated (120° C.) and pressurized (0.12 MPa) in the large-capacity tank 1, and thereby, the main sterilization treatment for killing the microorganisms is performed. After this, the seawater is stirred with stirring means 2 so that a nutrient salt concentration in the seawater after water vapor generated in the large-capacity tank 1 becomes water and drops becomes uniform in the entire area of the large-capacity tank 1. Accordingly, the main sterilization treatment step S4 is completed. Note that, in the case where the impurity removal treatment has not been performed at this point of time, the impurity removal treatment is performed subsequently.

Separately from the main sterilization treatment in the large-capacity tank 1, as indicated by reference symbol S5 in FIG. 2, several to tens of small-capacity resin bottles 3 are gathered at one place, and under this condition, the bottles 3 are irradiated with ultraviolet rays 4 at a time from outside. Thus, the entire inner surface of each of the bottles 3 is sterilized. In this case, the outer surface of each of the bottles 3 is also sterilized by irradiation with the ultraviolet rays 4, and when this treatment is performed, a cap of each of the bottles 3 may or may not be removed. Note that the bottles 3 are each made of polypropylene, polycarbonate, a tetrafluoroethylene/perfluoroalkyl vinyl ether copolymer (PFA), or the like. Thus, the bottle sterilization treatment step S5 is completed.

After that, as indicated by reference symbol S6 in FIG. 2, treated seawater subjected to the main sterilization treatment in the large-capacity tank 1 and the impurity removal treatment (standard seawater solution immediately after generation) is poured into the plurality of bottles 3 subjected to the sterilization treatment as described above, and each of the bottles 3 is hermetically sealed. Thus, the bottling step S6 is completed.

Next, as indicated by reference symbol S7 in FIG. 2, the outer surface of each of the bottles 3 after being hermetically sealed is covered with a film-like material 5 having a three-layer structure in which resin materials are provided on both front and back sides of a metal film (preferably an aluminum film) or a metal foil (preferably an aluminum foil) and sealed by reduced pressure suction. Thus, as indicated by reference symbol S71 in FIG. 2, the outer surface of the bottle 3 is sealed while being covered with a resin layer 5b, a metal layer 5a, and a resin layer 5c. The resin materials (resin layers 5b, 5c) are each made of a polymer film such as a PET film (polyethylene terephthalate). In addition, the film-like material 5 is produced by forming a metal film on the surface of a resin film by vapor deposition or the like or coating a metal foil with a resin. Note that any one or both of the resin layers may be formed of a plurality of layers including different kinds of polymer films or the like.

Further, the film-like material 5 can be configured as a so-called stand bag capable of holding the bottle 3 while allowing the bottle 3 to stand. Thus, the metal sealing step S7 is completed.

The standard seawater solution produced through the above-mentioned steps exhibits the effect of being suitable for long-term storage for the following reason.

That is, first, the standard seawater solution has been subjected to the metal sealing step S7. Therefore, even when the standard seawater solution sealed in the bottle 3 after the metal sealing step S7 is stored for a long period of time such as several years, its salt content and nutrient salt concentration hardly change because the metal film (aluminum film) or the metal foil (aluminum foil) is excellent in light-blocking property, moisture-proof property, and gas barrier property, and has property of preventing moisture from leaking outside.

Figure 3:
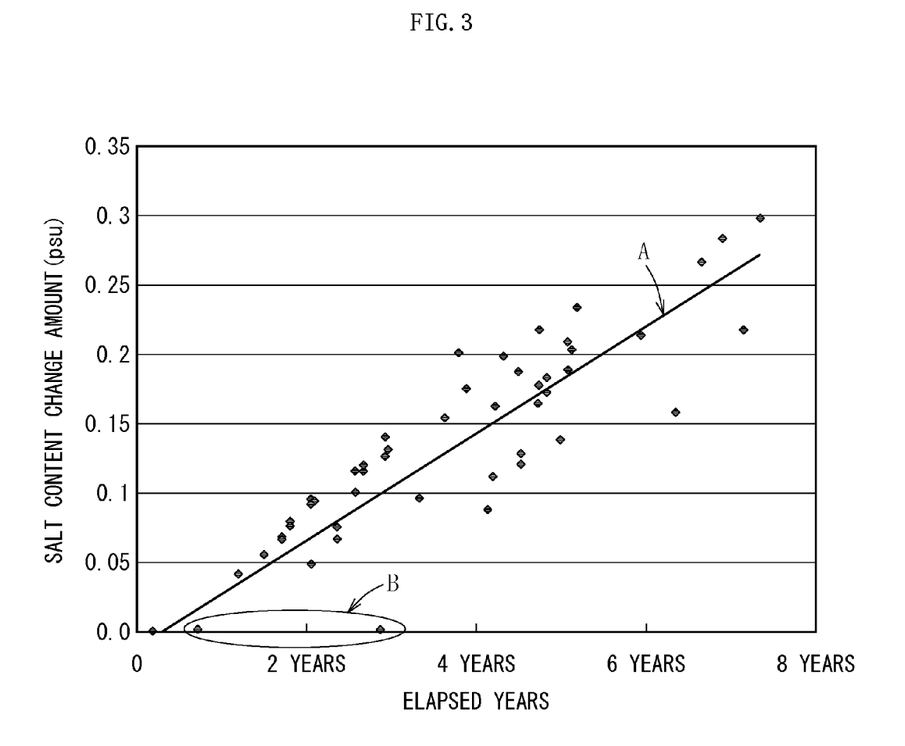
FIG. 3 is a graph showing effects obtained by performing the method of producing a standard seawater solution for nutrient salt measurement according to the embodiment of the present invention.
Figure 4:
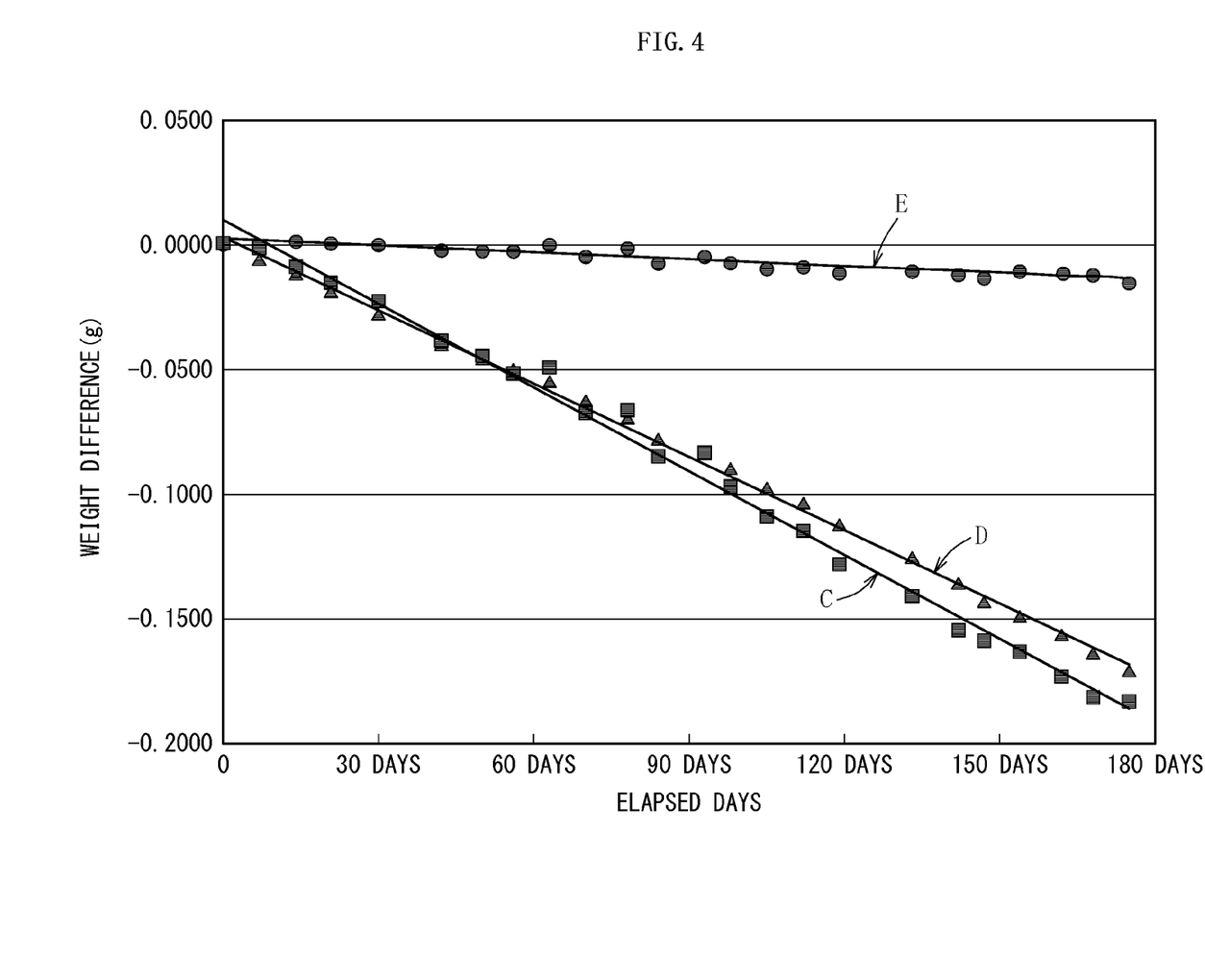
FIG. 4 is a graph showing effects obtained by performing the method of producing a standard seawater solution for nutrient salt measurement according to the embodiment of the present invention.

The above-mentioned effect is verified by graphs of FIGS. 3 and 4 showing results of experiments conducted by the inventors of the present invention. Specifically, the graph of FIG. 3 shows a salt content change amount of the standard seawater solution in the bottle with respect to elapsed years in the case where the bottle sealed after the metal sealing step S7 is stored at room temperature. As is understood from the graph, in the case where the outer surface of the bottle is sealed by reduced pressure suction with a film-like material made of polyethylene as in a conventional case, as represented by a straight line (straight line obtained by a least-square method) indicated by reference symbol A, the salt content increases gradually along with the elapsed years. In contrast, in the case where the outer surface of the bottle is sealed by reduced pressure suction with a film-like material including a metal layer (aluminum layer), as indicated by reference symbol B, the change in salt content was zero or substantially zero. Note that each on the measurement points displayed on the graph indicates an average of values measured with respect to tens of bottles. Further, the number of measurement points displayed in an area indicated by reference symbol B is small because three years have not elapsed after the start of the experiment.

Further, the graph of FIG. 4 shows a weight change of the standard seawater solution in the bottle with respect to elapsed days in the case where the sealed bottle after the metal sealing step S7 is held at 10° C. for 1 hour, then heated to 40° C. over 1 hour, held at 40° C. for 1 hour, and then cooled to 10° C. over 1 hour, and this process is repeatedly performed for 175 days and a weight change is measured every other week. In this graph, a straight line (straight line obtained by a least-square method) indicated by reference symbol C represents a result in the case where the bottle is exposed to ambient air without sealing the outer surface of the bottle; a straight line (straight line obtained by a least-square method) indicated by reference symbol D represents a result in the case where the outer surface of the bottle is sealed by reduced pressure suction with a film-like material made of polyethylene as in a conventional case; and a straight line (straight line obtained by a least-square method) indicated by reference symbol E represents a result in the case where the outer surface of the bottle is sealed by reduced pressure suction with a film-like material including a metal layer (aluminum layer). As is understood from the graph, the weight of the standard seawater solution decreases significantly along with the elapsed days in the straight lines C and D, whereas the weight of the standard seawater solution hardly changes and merely decreases slightly even when days have elapsed in the straight line E.

This shows the following: in the case where the outer surface of the bottle is sealed by reduced pressure suction with the film-like material including a metal layer (aluminum layer), mainly moisture in the standard seawater solution in the bottle is hardly evaporated, and hence the salt content and nutrient salt concentration of the standard seawater solution hardly change, whereas in the case of another procedure, a large amount of mainly moisture in the standard seawater solution in the bottle is evaporated, and hence the salt content and nutrient salt concentration of the standard seawater solution increase significantly. Thus, it can be understood that, in the case where the outer surface of the bottle is sealed by reduced pressure suction with a film-like material having a metal layer (aluminum layer), a change in nutrient salt concentration of the standard seawater solution in the bottle is very small compared with those of the other cases.

On the other hand, the standard seawater solution obtained by performing the respective steps S1 to S8 has been subjected to the bottle sterilization treatment step S5. Therefore, if at least the entire inner surface of an empty bottle is sterilized with ultraviolet rays in the step S5, after the standard seawater solution is sealed in the bottle, the following problem is avoided: microorganisms propagate in the bottle to decrease the nutrient salt concentration of the standard seawater solution. Accordingly, even in the case where the standard seawater solution is sealed in the bottle and stored for a long period of time, the nutrient salt concentration of the standard seawater solution does not increase improperly, and the properties of the standard seawater solution can be kept stable desirably.

REFERENCE SIGNS LIST 1 large-capacity tank
3 bottle
4 ultraviolet ray
5 film-like material including metal foil or metal film
5a metal layer (metal film or metal foil)
5b resin layer (resin material)
5c resin layer (resin material)
S2 impurity removal step
S4 main sterilization treatment step
S5 bottle sterilization treatment step
S6 bottling step
S7 metal sealing step

The invention claimed is:

1. A method of producing a standard seawater solution for nutrient salt measurement which is to be used as an indicator for measuring a nutrient salt concentration of a seawater sample and which uses seawater as a material, the method comprising at least:
   an impurity removal treatment step of removing an impurity from a seawater sample containing a nutrient salt;
   a main sterilization treatment step of killing a microorganism in the seawater sample;
   a bottling step comprising pouring the seawater sample which has been treated into a resin bottle and hermetically sealing the resin bottle; and
   a sealing step comprising covering an entire outer surface of the resin bottle after the hermetic sealing with a film material including a metal film or a metal foil and sealing the resin bottle therein by reduced pressure suction,
   wherein, before the bottling step is performed, a bottle sterilization treatment step comprising sterilizing at least an entire inner surface of the resin bottle with ultraviolet rays is performed, and
   wherein the bottle sterilization treatment step, the main sterilization treatment step, the bottling step and the sealing step are performed so that, in a case in which the resin bottle which has been hermetically sealed is stored at room temperature, a salt content change amount based on a numerical range of a salt content of 0 to 0.35 psu of the standard seawater solution in the resin bottle is zero or substantially zero at a time when two years have elapsed.

2. A method of producing a standard seawater solution for nutrient salt measurement according to claim 1, wherein the metal film or the metal foil of the film material comprises an aluminum film or an aluminum foil.

3. A method of producing a standard seawater solution for nutrient salt measurement according to claim 1, wherein the film material has a multi-layer structure in which a resin material is provided on each of a front side and a back side of the metal film or the metal foil.

4. A method of producing a standard seawater solution for film nutrient salt measurement according to claim 2, wherein the film material has a multi-layer structure in which a resin material is provided on each of a front side and a back side of the metal film or the metal foil.

* * * * *